(12) United States Patent
Crawford (10) Patent No.: US 11,878,155 B2
(45) Date of Patent: Jan. 23, 2024

(54) PASSIVE INTEGRATED SAFETY DEVICE AND AN INJECTION DEVICE COMPRISING THIS PASSIVE INTEGRATED SAFETY DEVICE

(71) Applicant: Becton Dickinson France, Le Pont de Claix (FR)

(72) Inventor: Jamieson Crawford, Hagersten (SE)

(73) Assignee: Becton Dickinson France, Le Pont de Claix (FR)

( * ) Notice: Subject to any disclaimer, the term of this patent is extended or adjusted under 35 U.S.C. 154(b) by 65 days.

(21) Appl. No.: 16/755,924

(22) PCT Filed: Oct. 17, 2018

(86) PCT No.: PCT/EP2018/078462
§ 371 (c)(1),
(2) Date: Apr. 14, 2020

(87) PCT Pub. No.: WO2019/077008
PCT Pub. Date: Apr. 25, 2019

(65) Prior Publication Data
US 2020/0297939 A1    Sep. 24, 2020

(30) Foreign Application Priority Data
Oct. 18, 2017  (EP) .................................... 17196990

(51) Int. Cl.
*A61M 5/32* (2006.01)
(52) U.S. Cl.
CPC .......... *A61M 5/3245* (2013.01); *A61M 5/326* (2013.01); *A61M 5/3271* (2013.01);
(Continued)
(58) Field of Classification Search
CPC ................ A61M 5/326; A61M 5/3245; A61M 2005/3267
See application file for complete search history.

(56) References Cited

U.S. PATENT DOCUMENTS 3,354,881 A   11/1967  Bloch
4,775,369 A * 10/1988  Schwartz .............. A61M 5/326
                                                            604/263
(Continued)

FOREIGN PATENT DOCUMENTS

CN    101563124 A    10/2009
CN    102753222 A    10/2012
(Continued)

OTHER PUBLICATIONS

Meenakshi, Syste. Review on Sterilization Methods, Jun. 2015, International Journal of ChemTech Research, vol. 8, 897-911 (Year: 2015).*

*Primary Examiner* — Nathan R Price
*Assistant Examiner* — Tania Ismail
(74) *Attorney, Agent, or Firm* — The Webb Law Firm (57) ABSTRACT

This passive safety device comprises an inner needle shield having a proximal end configured to be sealed to a tip of an injection device, a distal portion configured to be pricked by a needle in a pre-use position and pierced by the needle in an injection position, and an energy storage portion configured to accumulate energy as the passive safety device passes from the pre-use position to the injection position and release energy as the passive safety device passes from the injection position to a safety position. The passive safety device further comprises a sleeve surrounding the proximal end, an outer needle shield having a proximal end slidably attached to the sleeve so that the outer needle shield is movable relative to the sleeve, and a lock configured to lock the outer needle shield in the safety position.

15 Claims, 2 Drawing Sheets (52) U.S. Cl.
CPC ............... *A61M 2005/3247* (2013.01); *A61M 2005/3263* (2013.01); *A61M 2005/3267* (2013.01)

(56) References Cited

U.S. PATENT DOCUMENTS

| | | | |
|---|---|---|---|
| 5,688,241 A * | 11/1997 | Asbaghi | A61M 5/326 604/110 |
| 5,885,255 A | 3/1999 | Jaeger, Jr. et al. | |
| 6,387,078 B1 * | 5/2002 | Gillespie, III | A61M 5/2066 604/181 |
| 8,052,653 B2 | 11/2011 | Gratwohl et al. | |
| 9,694,141 B2 | 7/2017 | Slemmen et al. | |
| 11,007,327 B2 | 5/2021 | Bengtsson et al. | |
| 2003/0168366 A1 | 9/2003 | Hirsiger et al. | |
| 2012/0041368 A1 * | 2/2012 | Karlsson | A61M 5/326 604/111 |
| 2013/0018310 A1 | 1/2013 | Boyd et al. | |
| 2013/0218092 A1 | 8/2013 | Davies et al. | |
| 2014/0228772 A1 * | 8/2014 | Ward | A61M 5/3245 604/198 |
| 2014/0243755 A1 | 8/2014 | Slemmen et al. | |
| 2016/0346483 A1 * | 12/2016 | Fourt | A61M 5/3202 |
| 2017/0361029 A1 * | 12/2017 | Benito | A61M 5/20 |

FOREIGN PATENT DOCUMENTS

| | | | | |
|---|---|---|---|---|
| CN | 103282068 A | 9/2013 | | |
| CN | 103957971 A | 7/2014 | | |
| CN | 103957972 A | 7/2014 | | |
| CN | 104768598 A | 7/2015 | | |
| DE | 102006041810 A1 | 3/2008 | | |
| EP | 2635334 B1 | 8/2014 | | |
| EP | 2911724 B1 | 7/2017 | | |
| WO | WO-9531235 A1 * | 11/1995 | ............ | A61M 5/002 |
| WO | 2011098831 A1 | 8/2011 | | |
| WO | WO-2017158805 A1 * | 9/2017 | ............ | A61M 5/329 |

\* cited by examiner

PASSIVE INTEGRATED SAFETY DEVICE AND AN INJECTION DEVICE COMPRISING THIS PASSIVE INTEGRATED SAFETY DEVICE

CROSS-REFERENCE TO RELATED APPLICATIONS

This application is the United States national phase of International Application No. PCT/EP2018/078462 filed Oct. 17, 2018, and claims priority to European Patent Application No. 17196990.0 filed Oct. 18, 2017, the disclosures of which are hereby incorporated by reference in their entirety.

BACKGROUND OF THE INVENTION

Field of the Invention

The present invention to a passive needle safety device and an injection device, such as a prefilled syringe, comprising this passive needle safety device.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to the passive safety device or injection device of the invention, and the "proximal direction" is to be understood as meaning the opposite direction to said direction of injection, that is to say the direction towards the user's hand.

Description of Related Art

Injection devices, such as syringes, are usually furnished at their distal end with an injection needle that is designed to be inserted into the skin of a patient, and through which the product to be injected passes to an injection site. These syringes are usually furnished with a piston rod whose distal end comprises a piston which, during the injection phase and under the action of a distal pressure exerted by the user on the piston rod, pushes the product through the injection needle.

A usual problem presented by the injection devices equipped with a needle is the risk of accidental needle stick likely which may occur after the injection. In order to minimize this risk, it is known to furnish the syringes with a safety device which is intended to protect the needle after injection: this safety device may for example comprise a sleeve sliding relative to the syringe and required to cover the needle after the injection and the withdrawal of the needle from the injection site.

Some of these safety devices need to be activated by the user, that is to say that they require the user to undertake a specific action so as to be triggered and the needle thus be protected. In contrast to these active safety devices, some passive safety devices have been developed. A safety device is called passive when there is no need for a user to perform any action to ensure that the needle of the injection device is protected.

Document WO2011098831 discloses such a passive safety device. This passive safety device has the advantage of trying to avoid the so-called pop-off phenomenon during a sterilization process. This safety device comprises a soft rubber cover which is penetrated by the tip of the needle in order to prevent drug leakage. The safety device further includes a sleeve which is axially slidable between a needle protecting position and a non-protecting position. The proximal part of this sleeve is configured to deform radially outwardly so as to reach the non-protecting position. This deformation enables to store energy so that the proximal part of said sleeve acts as a spring urging the whole sleeve back to its initial protecting position once the needle is removed from the injection site.

However, the soft rubber cover needs to be removed and discarded before performing an injection.

Furthermore, in order to achieve an effective spring effect, the proximal part of the sleeve needs to be deformed at its greatest extent. This involves that the needle to be inserted a quite long distance into the injection site. This may be stressful or harmful for a user.

Besides, as noted above, the proximal part of the sleeve is configured to extend radially outwardly. This outward deformation renders the safety device quite radially cumbersome. Moreover, deformation of the sleeve is visible and may worry a user.

It should also be noted that the sleeve is likely made of a plastic material. However, plastic materials tend to lose their resiliently deformation abilities over time. After a long storage period, the fingers may thus lose some of their spring effect and the sleeve may thus not protect the needle as reliably as expected.

SUMMARY OF THE INVENTION

An aspect of the invention is a passive needle safety device which addresses the aforementioned drawbacks, that is to say a passive safety device which eliminates the need to remove and discard a needle plug or cover, which eliminates a pop-off effect during the sterilization process, and which is also compact, easy to use and to manufacture.

An aspect of the invention is a passive safety device comprising:

- an inner needle shield having a proximal end, said proximal end being configured to be sealed to a tip of an injection device, a distal portion, said distal portion being configured to be pricked by a needle in a pre-use position of the passive safety device and pierced by the needle in an injection position of the passive safety device, and an energy storage portion configured to accumulate energy as the passive safety device passes from the pre-use position to the injection position and to release energy as the passive safety device passes from the injection position to a safety position,
- a sleeve surrounding at least the proximal end of the inner needle shield;
- an outer needle shield having a proximal end slidably attached to the sleeve so that the outer needle shield is movable relative to the sleeve,
- locking means configured to lock the outer needle shield when the passive safety device reaches the safety position, and
- wherein the inner needle shield is configured to move the outer needle shield distally as the energy storage portion releases its stored energy.

The passive safety device according to the invention consequently forms an integrated passive safety needle shield. Indeed, the safety device is devoid of any removable part such as a closure cap or plug which needs to be discarded before performing an injection operation.

The passive integrated safety device may be then placed in three positions:

a pre-use position wherein the outer needle shield and the inner needle shield are extended in order to cover the needle. In this position, the needle is pricked in the distal end of the inner needle shield so that the liquid in the syringe cannot flow outside the syringe;

an injection position wherein the outer needle shield and the inner needle shield are retracted in order to expose the needle. In this position, the inner needle shield is pierced by the needle. The energy storage portion is compressed and stores energy as a spring;

a safety position wherein the outer needle shield and the inner needle shield at least partially extend back in order to cover the needle again. The inner needle shield is configured to push distally the outer needle shield from the injection position to the safety position. In other words, at the end of the injection, the outer needle shield is moved distally from the injection position to the safety position under the bias of the inner needle shield.

Conversely, the outer needle shield is preferably configured to push proximally the inner needle shield from the pre-use position to the injection position. In other words, the inner needle shield is retracted from the pre-use position to the injection position under the force of the outer needle shield.

The outer needle shield slides along the sleeve and the inner needle shield deforms so that the needle pierces the inner needle shield and extends outside the safety device in order to permit the injection be performed.

Moreover, the inner needle shield forms a permanently attached needle plug, which eliminates a pop-off phenomenon during steam sterilization.

The inner needle shield acts as a spring mechanism, due to its resiliently deformable intermediate portion. As a matter of fact, after injection, as the user withdraws the device from the patient's skin, the inner needle shield expands, releasing the stored energy, which causes the outer needle shield to automatically push forward. This allows the outer needle shield to cover back the needle once the injection operation is completed. Once in safety position, the outer needle shield then protects a user from an accidental needle stick.

As a result, the passive integrated safety device according to the invention uses the inner needle shield both as a sealing component and as a spring mechanism. This provides a compact and easy to manufacture safety device.

In embodiments, the outer needle shield comprises a tubular intermediate portion surrounding the inner needle shield.

As a result, the inner needle shield is protected. Besides, the outer needle shield may be configured to hide the inner needle shield, so that a user is not frightened. For instance, the outer needle shield and more precisely its tubular intermediate portion may be opaque or translucent.

In embodiments, the outer needle shield comprises a distal end configured to exert a proximal pressure on the distal portion of the inner needle shield.

Therefore, a proximal movement of the outer needle shield entails a proximal movement of the distal portion of the inner needle shield as the passive safety device moves from the pre-use position to the injection position.

In embodiments, the distal end of the outer needle shield has a proximal pushing surface which partially covers a distal face of the distal portion of the inner needle shield.

The outer needle shield therefore exerts an axial pressure on the inner needle shield when moved proximally. An axial pressure exerted on the distal portion of the inner needle shield by the outer needle shield provides a more efficient piercing of said distal portion by the needle without coring.

In embodiments, the distal end of the outer needle shield defines an opening configured to allow passage of the needle after the needle pierces the distal portion of the inner needle shield.

This provides an equally distributed pressure around the opening and around the part of the distal portion which is going to be pierced by the needle. As a result, a coring effect is prevented.

In embodiments, the distal end of the outer needle shield leans against the distal portion of the inner needle shield.

This may at least occur when the passive safety device is in the pre-use position. As a result, deformation of the inner needle shield is immediate from the moment that the outer needle shield begins to slide proximally. The spring effect provided by the deformation of the inner needle shield is thus immediately generated. This provides a safer safety device. The distal end of the outer needle shield preferably permanently contacts the distal portion of the inner needle shield.

In embodiments, in the safety position, the energy storage portion remains in an energy releasing state.

In embodiments, the inner needle shield comprises a distal pushing surface configured to exert a distal pressure on the outer needle shield in order to provide a safer deployment of the outer needle shield from the injection position to the safety position.

In the safety position, a distal end of the inner and outer needle shields preferably extend distally beyond a distal end of the needle. In the safety position, the needle is preferably contained within the distal portion of the inner needle shield.

In embodiments, the sleeve comprises guiding means configured to guide the movement of the outer needle shield along the sleeve. The guiding means may be configured to guide the outer needle shield firstly from the pre-use position to the injection position and secondly from the injection position to said safety position. The guiding means may comprise a guiding slot, for example provided on the sleeve, and a guiding pin, for example secured to the outer needle shield. The guiding pin is configured to slide inside the guiding slot. The slot may comprise a first straight track, having a distal end and a proximal end, and a second track extending obliquely relative to said first track. The second track may have a proximal end leading into said first track and a distal end opposite said proximal end. In the pre-use position, the guiding pin may be in the distal end of said second track. In the injection position, the guiding pin may be in the proximal end of said first track. In the safety position, the guiding pin may be in the distal end of said first track.

In embodiments, the safety device comprises maintaining means configured to maintain the outer needle shield in the pre-use position until a predetermined proximal force is exerted on the outer needle shield.

As a result, the outer needle shield does not inadvertently leave the pre-use position and the needle therefore cannot inadvertently pierce the inner needle shield. This helps keeping the needle sealed inside the distal portion of the inner needle shield until an injection process begins.

For example, said maintaining means may comprise a slope surface configured to resist a movement of the outer needle shield from the pre-use to the injection position as long as a sufficient force is not applied to the outer needle shield and to let the outer needle shield go by when the force applied to the outer needle shield exceeds a predetermined threshold. This slope member may be located in the distal end of the second track.

In embodiments, the safety device comprises anti-return means configured to prevent the outer needle shield to move back to the pre-use position after the outer needle shield leaves the pre-use position.

This makes sure that the outer needle shield is reliably moved towards the safety position so as to reliably prevent needle stick injuries.

For example, the anti-return means may comprise the above mentioned second track which is oblique relative to the first track which extends in the longitudinal direction of the safety device. The anti-return means may also comprise an abutment surface configured to prevent return of the guiding pin in the distal end of the second track. The abutment surface may be proximally adjacent to the slope surface. The slope surface and the abutment surface may thus be two different surfaces of a ratchet element.

The locking means may comprise a ratchet element which may be located at a distal end of the first track. This ratchet element comprises a distal abutment surface which prevents the guiding pin from leaving the distal end of the first track. The ratchet element may comprise a proximal slope surface which is configured to help the guiding go by the ratchet element and reach the distal end of the first track. The slope surface may be adjacent to the abutment surface.

The inner needle shield is preferably made of a resiliently deformable material. This resiliently deformable material is able to partially or totally recover its initial shape after having been deformed. This resiliently deformable material may be coated or not. This resiliently deformable material preferably presents a shore A hardness between 10 and 60, and more preferably between 30 and 60.

The inner needle shield is preferably made of rubber. This rubber may be coated or not. This rubber preferably presents a having a shore A hardness between 10 and 60 and more preferably between 30 and 60.

The energy storage portion may be made of any material of the group comprising rubber, silicone or TPE material or a combination thereof.

In embodiments, the energy storage portion of the inner needle shield is axially compressible.

As a result, deformation of the inner needle shield does not entail a radial extension of the safety device.

The energy storage portion is configured to surround the needle.

In embodiments, the energy storage portion of the inner needle shield is configured to form at least one fold when the distal portion is moved proximally.

The energy storage portion is preferably accordion-shaped when compressed. Having an energy storage portion which forms at least one fold when compressed, or which is configured to fold-up in an concertinaed manner, enables to improve compactness of the passive safety device in the injection position.

In embodiments, the energy storage portion of the inner needle shield is tubular and defines an internal cavity.

This provides a compact safety device.

In embodiments, the energy storage portion of the inner needle shield comprises folding slots configured to give the energy storage portion an accordion shape when being deformed.

This helps the energy storage portion to fold-up like an accordion and thus remain compact when being deformed.

The height of these folds may preferably be defined so that the deformed intermediate portion does not contact the needle.

The distal portion of the inner needle shield may have a length comprised between 3 and 12 mm.

This limits the risk of coring as the needle pierces the distal portion during the injection process.

In embodiments, the distal portion of the inner needle shield comprises a resiliently deformable material.

In embodiments, the energy storage portion of the inner needle shield comprises a resiliently deformable material.

In embodiments, the distal portion of the inner needle shield comprises a material whose hardness is comprised between 30 and 70 shore A and more preferably between 30 and 60 shore A. This makes it easier for the needle to pierce said distal portion while avoiding a coring effect.

In embodiments, the energy storage portion of the inner needle shield comprises a material whose hardness is comprised between 10 and 60 shore A and more preferably between 30 and 60 shore A.

In embodiments, the sleeve comprises a proximal part configured to extend around the distal tip of an injection device, and a distal part configured to distally extend beyond said distal tip, said distal part defining a lateral containment wall surrounding at least a part of the energy storage portion of the inner needle shield.

This forces said energy storage portion to deform inwardly.

In embodiments, the sleeve is fixed relative to the inner needle shield. This provides a reliable safety device. For example, the sleeve may be glued, clipped or may be fixed due to friction forces on the inner needle shield.

In embodiments, the inner needle shield comprises a material which is permeable to a sterilization gas.

This allows sterilization while the safety device is mounted on the distal tip of an injection device, thus avoiding a pop-off effect. To that end, the inner needle shield may preferably comprise a rubber material.

In embodiments, the outer needle shield is permeable to a sterilization gas.

In embodiments, the inner needle shield is soft in order to be pierced by the needle and in order to resiliently deform, while the outer needle shield is rigid in order to press and protect the inner needle shield.

The inner needle shield can be made of a material or of a combination of materials of the group comprising rubber, silicone and TPE materials.

In embodiments, the outer needle shield comprises a plastic material.

The outer needle shield can be made of a material or of a combination of material of the group comprising rubber, silicone and TPE materials.

In embodiments, the sleeve comprises a plastic material.

Another aspect of the invention is an injection device comprising a barrel, a distal tip, a needle supported by said distal tip and the above-described passive safety device mounted onto the distal tip.

The injection device may be a prefilled syringe.

In embodiments, the proximal end of the inner needle shield is sealed to the distal tip of the barrel.

As a result, the inner needle shield, which acts as a spring mechanism, also acts as a sealing element so as to keep the injection device be sterilized.

In embodiments, the inner needle shield is sealed on the distal tip by gluing and/or by clamping.

For example, the inner needle shield is sealed on the distal tip by using the sleeve in order to clamp the inner needle shield against the distal tip. Therefore, the sleeve may be configured to surround and clamp the proximal end of the inner needle shield around the distal tip of the barrel.

As a result, the sleeve compresses the distal end of the inner needle shield over the distal tip of the barrel and therefore provides a tight seal around said distal tip. For example, the sleeve may have an internal diameter which is lower than an external diameter of the inner needle shield.

This length may be preferably equal to or greater than the distance between a distal end of the needle and a distal face of the distal portion. In other words, in the pre-use position, the distance between a distal end of the needle and a distal surface of the distal portion of the inner needle shield is less than 10 mm.

As a result, the distance that the needle needs to cover so as to pierce the distal portion remains low, which limits coring. In the pre use position, the needle is partially inserted in the distal portion of the inner needle shield such that a first part of the distal portion of the inner needle shield is pierced by the needle while a second part of the distal portion of the inner needle shield is not yet pierced by the needle, said second part having a thickness comprised between 0.4 mm and 3 mm. In embodiments, the injection device comprises retaining means configured to prevent withdrawal of the safety device from the distal tip of the barrel.

This provides a safer injection device.

BRIEF DESCRIPTION OF THE DRAWINGS

The invention and the advantages arising therefrom will clearly emerge from the detailed description that is given below with reference to the appended drawings as follows.

DESCRIPTION OF THE INVENTION

Figure 1A:
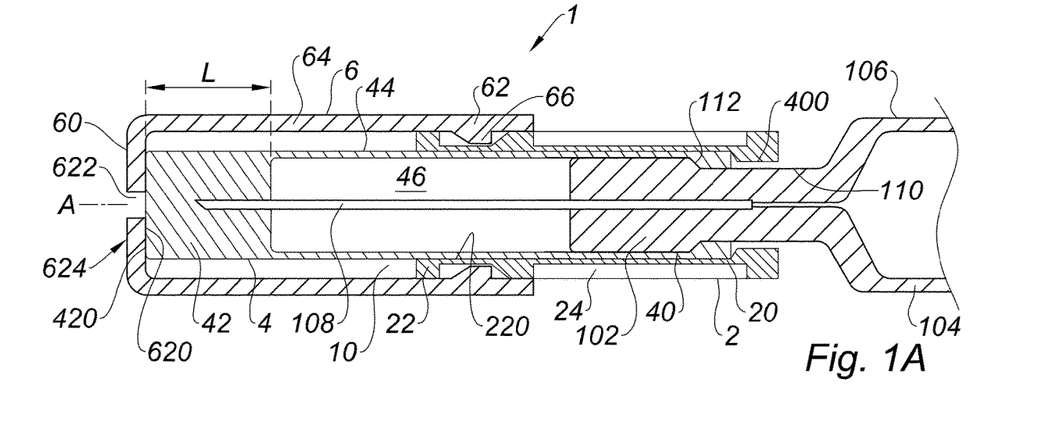
FIGS. 1A to 1C are cross section views of a safety device according an embodiment of the invention, in different positions.
Figure 1B:
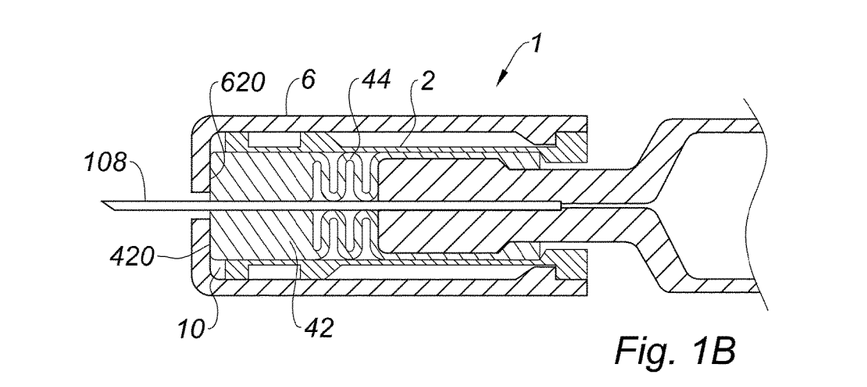
Figure 1C:
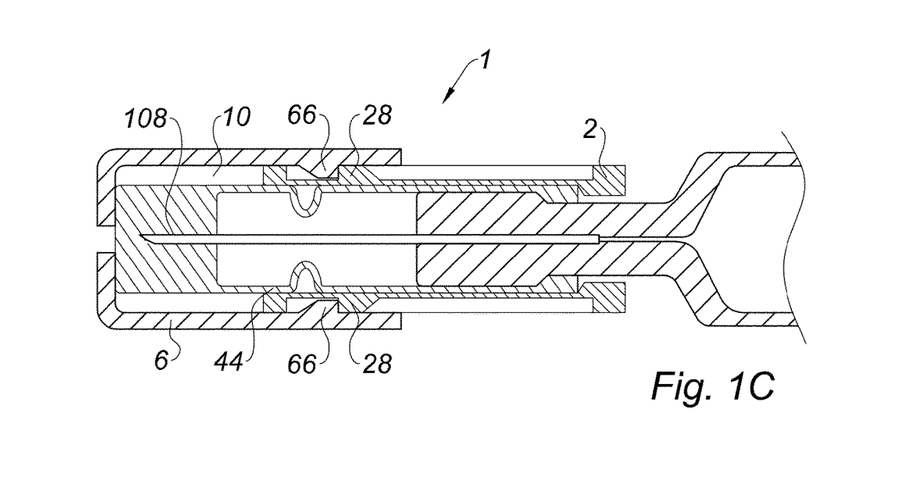

With reference to FIGS. 1A to 1C is shown a safety device 1 of the invention. The safety device 1 is intended to be mounted on a distal tip 102 of a barrel 104 of a syringe 106 so as to surround a needle 108 extending from said distal tip 102. The safety device 1 is aimed at maintaining sterility of the needle 108 and preventing leakage from the needle 108 in a pre-use condition, allowing insertion of the needle 108 into an injection site during an injection operation, and preventing a needle stick injury in a post-use condition where the injection operation is completed.

In this application, by "passive safety device" it is meant a needle safety device which does not require the user to undertake any action after injection so as to make the needle be protected after removal of the needle from an injection site.

In this application, by "integrated safety device" it is meant a safety device which does not comprise any component which needs to be discarded in order to enable the user to perform an injection operation.

The passive integrated safety device 1 comprises a sleeve 2, a soft inner needle shield 4 and a rigid outer needle shield 6. The passive safety device 1 may be moved into three positions: a pre-use position (FIG. 1A) wherein the outer needle shield 6 is in its most distal position relative to the sleeve 4, an injection position (FIG. 1B) wherein the outer needle shield 6 is in its most proximal position relative to the sleeve 2, and a safety position (FIG. 1C) wherein the outer needle shield 6 is distally located away from the injection position.

The passive safety device 1 also comprises locking means configured to lock the rigid outer needle shield 6 in the safety position (FIG. 1C). The safety position may correspond to the pre-use position or preferably to an intermediate position located between the pre-use and injection positions. The locking means will be described in further details later.

The outer needle shield 6 has a proximal end 60, a distal end 62 opposite said proximal end 60, and an intermediate portion 64.

The inner needle shield 4 has a proximal end 40, a distal portion 42 opposite said distal end 40, and an intermediate energy storage intermediate portion 44 connecting the proximal end 40 and the distal portion 42.

The proximal end 40 of the inner needle shield 4 is configured to be tightly sealed onto the distal tip 102 of the syringe 106, so as to maintain sterility of the needle 108 in a pre-use condition. The proximal end 40 of the inner needle shield 4 may be sealed on the distal tip 102 by gluing. The proximal end 40 of the inner needle shield 4 may also be sealed on the distal tip 102 by clamping, for example by using the sleeve 2 in order to compress the inner needle shield 4 against the distal tip 102. The proximal end 40 of the inner needle shield 4 may be made of a resiliently deformable, such as rubber, so as to provide a tight seal around said distal tip 102.

Besides, the sleeve 2 may have an internal diameter which is lower than an external diameter of the proximal end 40 of the inner needle shield 4 so that the inner needle shield 4 is secured to the sleeve 4 when the sleeve 2 is mounted around the proximal end 40 of the inner needle shield 4.

The distal tip 102 of the syringe 106 may comprise a groove 110 or a proximally directed abutment surface 112, while the proximal end 40 of the inner needle shield 4 may comprise a complementarily shaped protrusion 400 or distally directed abutment surface 402. The groove 110, abutment surfaces 112, 402 and/or the protrusion 400 thus form retaining means configured to prevent accidental withdrawal of the safety device 1 from the distal tip 102.

The distal portion 42 of the inner needle shield 4 is configured to be pricked by a distal end of the needle 108 in the pre-use position in order to prevent drug leakage through the needle 108, and then be pierced by the needle 108 when an injection position is performed. The distal portion 42 of the inner needle shield 4 is thus movable relative to the proximal end 40 of the inner needle shield 4 between a pre-use position (FIG. 1A), wherein the distal portion 42 may be at its most distal position from the proximal end 40 of the inner needle shield 4 and is intended to be just pricked by the needle 108, and an injection position (FIG. 1B), wherein the distal portion 42 may be at its most proximal position from the proximal end 40 of the inner needle shield 4 and is intended to be totally pierced by the needle 108. Besides, the distal portion 42 of the inner needle shield 4 may be movable to a safety position (FIG. 1C), which may correspond to the pre-use position or which may be an intermediate position between the pre-use position and the injection position, wherein the distal portion 42 of the inner needle shield 4 is configured to distally extend beyond a distal end of the needle 108 in order to cover back the needle 108.

In the safety position, the distal end 60 of the outer needle shield 6, respectively the distal portion 42 of the inner needle shield 4, preferably extends distally beyond a distal end of the needle 108. Besides, in the safety position, the distal end of the needle 108 is preferably contained within the distal portion 42 of the inner needle shield 4.

The distal portion 42 of the inner needle shield 4 may be formed of a soft material, preferably a resiliently deformable material, such as rubber. The material of the distal portion 42 of the inner needle shield 4 may preferably have a hardness comprised between 10 and 60 Shore A so as to prevent a coring effect when the distal portion 42 of the inner needle shield 4 is being pierced by the needle 108.

The part of the distal portion 42 which is intended to be pricked by the needle 108 in a pre-use position may be longer than that which is intended to be pierced by the needle 108. The energy storage portion 44 may be a tubular, for example cylindrical, portion configured to surround the needle 108. Accordingly, in a pre-use condition, the inner needle shield 4 defines an internal cavity 46 wherein the needle 108 is intended to extend and be kept sterile.

The energy storage portion 44 is configured to accumulate energy as the distal portion 42 of the inner needle shield 4 is being moved from the pre-use position to the injection position. For example, the energy storage portion 44 may be advantageously resiliently deformable so as to act as a spring which is able to urge distally the distal portion 42 of the inner needle shield 4 from the injection position towards the safety position. When the passive safety device 1 is in the pre-use position, the energy storage portion 44 is preferably in a rest state (FIG. 1A). When the safety device 1 is in the injection position, the energy storage portion 44 is preferably axially compressed (FIG. 1B). When the passive safety device 1 is in the safety position, the energy storage portion 44 is preferably axially extended (FIG. 1C). In the safety position, the energy storage portion 44 may be in the same state as in the pre-use position, for instance not deformed or less deformed than in the injection position.

The energy storage portion 44 may thus be made of a resiliently deformable material, such as rubber or rubber or TPE material or a combination thereof.

The energy storage portion 44 is preferably configured to be axially compressible, so as to remain as compact as possible while being deformed. As shown on FIG. 1B, the energy storage portion 44 may be configured to form a collapsible accordion. The folds formed by the concertina-like compressed energy storage portion 44 may extend in the internal cavity 46 of the tubular inner needle shield 4. The internal cavity 46 of the inner needle shield 4 thus also defines an accommodation space wherein the tubular energy storage portion 44 can collapse.

The energy storage portion 44 may be configured not to contact the needle 108, whatever the deformation of the energy storage portion 44 is. As a result, the energy storage portion 44 remains remote from the needle 108 even in the injection condition.

The energy storage portion 44 may comprise folding slots or grooves (not illustrated) extending orthogonally to a longitudinal axis A of the safety device 1 and configured to give the energy storage portion 44 a predetermined wrinkled shape when being deformed. The height of the folds, that is to say the distance between slots or grooves, may preferably be less than half the width of the internal cavity 46 so that the deformed intermediate portion does not contact the needle 108

The inner needle shield 4 is configured to move the outer needle shield 4 from the injection position to the safety position as the energy storage portion 44 releases its stored energy. To that end, the distal portion 42 of the inner needle shield 4 may advantageously comprise a distal pushing surface 420 configured abut on the outer needle shield 6, more precisely on the distal end 60 of the outer needle shield 6.

In the safety condition, the energy storage portion 44 preferably remains in an energy releasing state, that is to say in a deformed state, so as to make the distal pushing surface 420 exert a distal pressure on the outer needle shield 6.

The inner needle shield 4 is advantageously made of a material which is permeable to a sterilization gas such as ethylene oxide (EtO). This allows sterilization while the safety device 1 is already mounted on the distal tip 102, thus avoiding a pop-off effect. For example, the inner needle shield 4 is made of a rubber material.

The intermediate portion 64 of the outer needle shield 6 may be tubular, for example cylindrical, so as to surround and thus protect the inner needle shield 4. The outer needle shield 6 and more precisely the intermediate portion 64 of said outer needle shield 6 may be opaque or translucent.

The distal end 62 of the outer needle shield 6 is configured to exert a proximal pressure on the distal portion 42 of the inner needle shield 4, so that proximal movement of the outer needle shield 6 from the pre-use position to the injection position entails proximal movement of the distal portion 42 of the inner needle shield 4, thereby also causing piercing of this distal portion 42 of the inner needle shield 4 by the needle 108 and deformation of the energy storage portion 44. To that end, the distal end 62 of the outer needle shield 6 may have a proximal pushing surface 620 which partially covers a distal face of the distal portion 42 of the inner needle shield 4, for example the distal pushing surface 420. The distal end 62 of the outer needle shield 6, especially its proximal pushing surface 620, may permanently contact a distal face of the distal portion 42 of the inner needle shield 4, whatever the position of the outer needle shield 6.

In order to provide a uniform pressure distribution and to allow passage of the needle through the distal end 62 of the outer needle shield 6, said distal end 62 may advantageously define a central opening 622. This central opening 622 is dimensioned so as to allow reliable passage of the needle 108 through the distal end 62 of the outer needle shield 6.

In order to protect the needle 108, the outer needle shield 6 is preferably rigid, more precisely more rigid than the soft inner needle shield 4. For example, the outer needle shield is made of a plastic material such as polypropylene, polyethylene, polycarbonate, POM, PBT, ABS or a combination thereof.

The proximal end 60 of the outer needle shield 6 is slidably attached to the sleeve 2 so that the outer needle shield 6 is axially movable relative to the sleeve 2, as will be described hereinafter in more details.

The safety device 1 may advantageously delimit an accommodation space 10 between the outer needle shield 6 and the inner needle shield 4 so that any contact and friction between the intermediate portion 64 of the outer needle shield 6 and a lateral wall of the distal portion 42 of the inner needle shield 4 or the energy storage portion 44 of the inner needle shield 4 is prevented The sleeve 2 is configured to surround at least the proximal end 40 of the inner needle shield 4. The sleeve 2 may therefore have a tubular shape, for example a cylindrical shape.

The sleeve 2 may advantageously comprise a proximal part 20 which surrounds the proximal end 40 of the inner needle shield 4. The sleeve 2 may also comprise a distal part 22 which may be configured to extend beyond the distal tip 102 of the syringe 106. This distal part 22 of the sleeve 2 comprises a lateral containment wall 220 which surrounds partially the energy storage portion 44 of the inner needle shield 4 in the pre-use condition, in order to force the energy storage portion 44 to deform inwardly when the distal portion 42 of the inner needle shield 4 is being moved to the injection position by the outer needle shield 6.

It is contemplated that the sleeve 2 is fixed relative to the inner needle shield 4. For example, the sleeve 2 may be glued or clipped on the inner needle shield 4. It is also possible that the inner needle shield 4 is friction-fitted inside the sleeve 2.

The sleeve 2 is preferably made of a plastic material, such as, for example, polypropylene or Polycarbonate, POM, PBT, ABS or a combination thereof.

Figure 2:
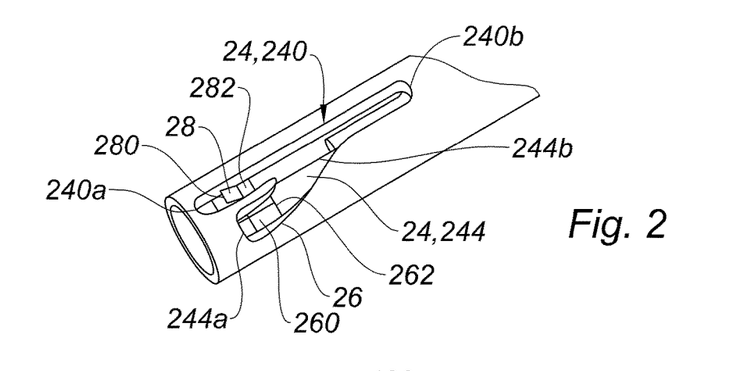
FIG. 2 is a perspective view of a part of a safety device according an embodiment of the invention.

With reference to FIG. 2, the sleeve 2 may comprise a guiding slot 24 and the outer needle shield 6 may comprise a guiding pin 66 configured to slide inside the guiding slot 24 in order to guide a sliding movement of the outer needle shield 6 relative to the sleeve 2. This guiding slot 24 and the guiding pin 66 thus form guiding means configured to guide the movement of the outer needle shield 6 along the sleeve 2 between the pre-use position and the injection position.

The guiding slot 24 may comprise a first track 240, said first track 240 having a closed distal end 240a and a closed proximal end 240b. The guiding slot 24 may also comprise a second track 244 which may have a closed distal end 244a and an open proximal end 244b leading into said first track 240, for example into an intermediate portion of said first track 240. The first track 240 may be parallel to the longitudinal axis A of the safety device, while the second track 244 at partly extends obliquely relative to the first track 240. In the pre-use position, the guiding pin 66 may be positioned in the distal end 244a of said second track 244 while in the injection position, the guiding pin 66 may be located in the proximal end 240b of said first track 240. In the safety position of the outer needle shield 6, the guiding pin 66 may be located in the distal end 240a of said first track 240. As a result, the guiding means are configured to guide the outer needle shield 6 firstly from the pre-use position to the injection position and secondly from the injection position to said safety position.

The sleeve 2 may comprise a distal slope surface 260 configured to resist a movement of the outer needle shield 6, especially of the guiding pin 66, from the pre-use to the injection position as long as a proximally directed force applied to the outer needle shield 6 remains lower than a predetermined threshold, and to let the outer needle shield 6 leave the pre-use position and move towards the injection position when the force applied to the outer needle shield 6 exceeds said predetermined threshold. This slope surface 260 may be located in the distal end 244a of the second track 244. This slope surface 260 and the guiding pin 66 thus form maintaining means configured to maintain the outer needle shield 6 in the pre-use position until a predetermined proximal force is exerted on the outer needle shield 6.

It is contemplated that the slope surface 260 may be part of a first ratchet element 26. This ratchet element 26 may also comprise a proximal abutment surface 262 configured to prevent return of the guiding pin 66 in the distal end 244a of the second track 224. The abutment surface 262 may be orthogonal to the longitudinal axis A of the safety device. The oblique arrangement of the second track 244, and/or the ratchet element 26, especially its abutment surface 262 may form anti-return means configured to prevent the outer needle shield 6 to move back to the pre-use position once the outer needle shield 6 has left this pre-use position.

The sleeve 2 may comprise a second ratchet element 28 which may be located at a distal end 240a of the first track 240. This ratchet element 28 comprises a distal abutment surface 280 which prevent the guiding pin 66 from leaving the distal end 240a of the first track 240 once the guiding has reached this distal end 240a. said distal abutment surface 280 may be orthogonal to a longitudinal axis A of the safety device 1. The ratchet element 28 may further comprise a proximal slope surface 282 which is configured to help the guiding pin 66 pass by the ratchet element 28 and reach the distal end 240a of the first track 240. The slope surface 282 may be adjacent to the abutment surface 280. As a result, the ratchet element 28, especially its abutment surface 280, keeps the outer needle shield 6 in the safety position and may thus form the locking means of the safety device 1.

The safety device 1 may preferably comprise abutting means configured to stop the proximal movement of the outer needle shield 6 relative to the sleeve 2 when the outer needle shield 6 reaches the injection position, so that a user knows when a plunger rod of the syringe 106 may be pushed in order to expel the product contained in the syringe 106. For example, said abutting means may comprise an abutment surface arranged in the sleeve 2 and against which the outer needle shield abuts when the outer needle shield 6 reaches the injection position. The abutting surface may be an end wall of the first track 240. As a result, the proximal end 240b of said first track 240 may form the abutting means.

The invention also relates to an injection device 100, such as syringe 106 or advantageously a pre-filled syringe 106, comprising a barrel 104 which defines a reservoir configured to contain an injectable product, a distal hub 102, a needle 108 supported by said distal tip 102 and the above described passive integrated safety device 1 mounted onto the distal tip 102. The distal tip 102 may be part of the distal end of the barrel 104 or it may be an element distinct from the barrel 104 which is fixed and/or connected to the distal end of the barrel 104, by any classical means, such as gluing, screwing, interlocking . . . . The distal end 40 of the inner needle shield 4 is sealed to the distal tip 102, for example by gluing or by clamping as already mentioned. The sleeve 2 may be fixed relative to the distal tip 102, the outer needle shield 6 is able to slide along the sleeve 2, and the inner needle shield 4 is deformable.

The needle 108 is pricked inside the distal portion 42 of the inner needle 4 shield over a length which is comprised between 3 and 12 mm. This length may be preferably equal to or greater than the distance separating a distal end of the needle 108 and a distal face of the distal portion 42 of the inner needle shield 4, that is to say equal or greater than the length of the not yet pierced part of the distal portion 42 of the inner needle shield 4.

Operation of the injection device is described below with reference to FIGS. 3A to 3D.

Figures 3A, 3B, 3C, 3D:
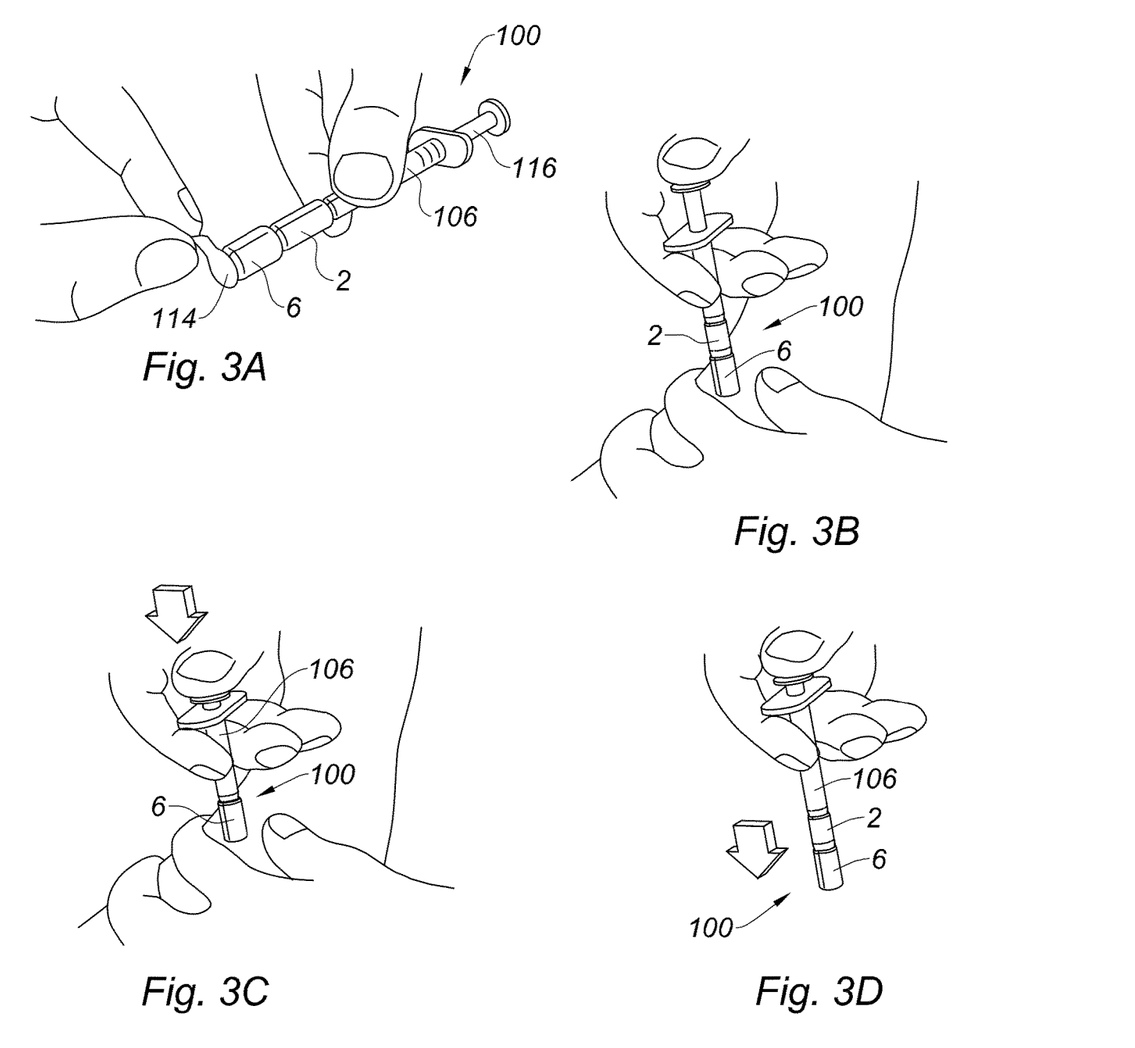
FIGS. 3A to 3D are perspective views of an injection device according to an embodiment of the invention, during different steps of an injection process.

With reference to FIG. 3A, a user may firstly remove a sterility label 114 which may be attached to the distal end 62 of the outer needle shield 6 to indicate that the sterility of the injection device 1 has been preserved, and that the outer needle shield 6 has not already been partially moved towards the injection position.

With reference to FIG. 3B, the injection device 100 is applied to the injection site, such as a patient's skin. More precisely, a distal face 624 of the distal end 62 of the outer needle shield 6 is positioned against the injection site. The user then pushes the syringe 106 towards the injection site with a sufficient force, which entails proximal movement of the outer needle shield 6 from the pre-use position towards the injection position. As a consequence, the distal end 62 exerts a proximal pressure on the distal portion 42 of the inner needle shield 4 whose energy storage portion 44 deforms as the outer needle shield 6 is being moved proximally towards the injection position. Meanwhile, the needle 108 pierces the distal portion 42 of the inner needle shield 4 and passes through the opening 622 of the outer needle shield 6, thereby entering the injection site.

With reference to FIG. 3C, the outer needle shield 6 has reached the injection position, its proximal movement being stopped by the sleeve 2 so that the user knows the needle 108 is fully advanced into the injection site. The distal portion 42 of the inner needle shield 4 is in the injection position while the energy storage portion 44 is compressed and ready to release its stored energy. The user can press a plunger rod 116 of the injection device 100 so as to expel the product contained in the barrel 104.

With reference to FIG. 3D, the product has been expelled. The user removes the injection device 100 from the injection site. The energy storage portion 44 starts releasing its stored energy, distally urging the distal portion 42 of the inner needle shield 4 back towards the safety position. The distal portion 42 of the inner needle shield 4 thereby pushes the distal end 62 of the outer needle shield 6 which thus slides back relative to the sleeve 2 from the injection position towards the safety position. The distal portion 42 finally covers the distal end of the needle 108 again and the outer needle shield 6 finally reaches the safety position where it is locked relative to the sleeve 2, thus forming a protective shell surrounding the inner needle shield 4 and the needle 8. The inner and outer needle shields 4, 6 therefore automatically deny access to the needle 108 and prevent accidental needle stick injuries.

It is to be understood that the invention is not limited to the above-described exemplary embodiments and includes any other alternative or equivalent embodiments. For instance, the passive safety device 1 could be devoid of maintaining means for temporarily maintaining the passive safety device in a pre-use condition. For instance, the distal end 62 of the outer needle shield 6 could have no proximal pushing surface 620, a lateral wall of the outer needle shield 6 being instead glued or secured to a lateral wall of the distal portion 42 of the inner needle shield 4.

The invention claimed is:

1. A passive safety device comprising:
 an inner needle shield having a proximal end, said proximal end being configured to be sealed to a tip of an injection device, a distal portion, said distal portion being configured to be pricked by a needle in a pre-use position of the passive safety device and pierced by the needle in an injection position of the passive safety device, and an energy storage portion configured to accumulate energy as the passive safety device passes from the pre-use position to the injection position and to release energy as the passive safety device passes from the injection position to a safety position,
 a sleeve surrounding at least the proximal end of the inner needle shield,
 an outer needle shield having a proximal end slidably attached to the sleeve so that the outer needle shield is movable relative to the sleeve,
 a lock configured to lock the outer needle shield when the passive safety device reaches the safety position, and
 wherein the inner needle shield is configured to move the outer needle shield distally as the energy storage portion releases its stored energy,
 wherein the sleeve comprises a distal part that extends beyond the tip of the injection device, said distal part defining a lateral containment wall surrounding at least a part of the energy storage portion of the inner needle shield, and
 wherein the lateral containment wall is configured to force the energy storage portion of the inner needle shield to deform inwardly when the distal portion of the inner needle shield is moved to the injection position.

2. The passive safety device according to claim 1, wherein the outer needle shield comprises a tubular intermediate portion surrounding the inner needle shield.

3. The passive safety device according to claim 1, wherein the outer needle shield comprises a distal end configured to exert a proximal pressure on the distal portion of the inner needle shield.

4. The passive safety device according to claim 3, wherein the distal end of the outer needle shield defines an opening configured to allow passage of the needle after the needle pierces the distal portion of the inner needle shield.

5. The passive safety device according to claim 3, wherein the distal end of the outer needle shield leans against the distal portion of the inner needle shield.

6. The passive safety device according to claim 1, wherein the inner needle shield comprises a resiliently deformable material.

7. The passive safety device according to claim 1, wherein the inner needle shield comprises a material whose hardness is comprised between 10 and 70 shore A.

8. The passive safety device according to claim 1, wherein the inner needle shield comprises rubber.

9. The passive safety device according to claim 1, wherein the energy storage portion of the inner needle shield is axially compressible.

10. The passive safety device according to claim 1, wherein the energy storage portion of the inner needle shield is configured to form at least one fold when the distal portion is moved proximally.

11. The passive safety device according to claim 1, wherein the energy storage portion of the inner needle shield is tubular and defines an internal cavity.

12. The passive safety device according to claim 1, wherein the inner needle shield is permeable to a sterilization gas.

13. The passive safety device according to claim 1, wherein the outer needle shield is permeable to a sterilization gas.

14. An injection device comprising a barrel comprising a distal tip, a needle supported by the distal tip of the barrel, and a passive safety device mounted onto the distal tip of the barrel, comprising:
 an inner needle shield having a proximal end, said proximal end being configured to be sealed to the distal tip of the barrel, a distal portion, said distal portion being configured to be pricked by a needle in a pre-use position of the passive safety device and pierced by the needle in an injection position of the passive safety device, and an energy storage portion configured to accumulate energy as the passive safety device passes from the pre-use position to the injection position and to release energy as the passive safety device passes from the injection position to a safety position,
 a sleeve surrounding at least the proximal end of the inner needle shield, an outer needle shield having a proximal end slidably attached to the sleeve so that the outer needle shield is movable relative to the sleeve, a lock configured to lock the outer needle shield when the passive safety device reaches the safety position, and wherein the inner needle shield is configured to move the outer needle shield distally as the energy storage portion releases its stored energy, wherein the sleeve comprises a distal part that extends beyond the distal tip of the barrel, said distal part defining a lateral containment wall surrounding at least a part of the energy storage portion of the inner needle shield, and wherein the lateral containment wall is configured to force the energy storage portion of the inner needle shield to deform inwardly when the distal portion of the inner needle shield is moved to the injection position.

15. The injection device according to claim 14, wherein the proximal end of the inner needle shield is sealed to the distal tip of the barrel.

\* \* \* \* \*